(12) United States Patent
Blake

(10) Patent No.: US 10,874,471 B2
(45) Date of Patent: Dec. 29, 2020

(54) CATHETER DRESSING SYSTEM

(71) Applicant: Luke Blake, Terre Haute, IN (US)

(72) Inventor: Luke Blake, Terre Haute, IN (US)

( * ) Notice: Subject to any disclaimer, the term of this patent is extended or adjusted under 35 U.S.C. 154(b) by 485 days.

(21) Appl. No.: 15/802,528

(22) Filed: Nov. 3, 2017

(65) Prior Publication Data
US 2019/0053868 A1 Feb. 21, 2019
US 2020/0022770 A9 Jan. 23, 2020

Related U.S. Application Data

(63) Continuation-in-part of application No. 15/377,146, filed on Dec. 13, 2016, now Pat. No. 10,117,717.

(51) Int. Cl.
*A61M 25/02* (2006.01)
*A61B 46/20* (2016.01)

(52) U.S. Cl.
CPC ............ *A61B 46/20* (2016.02); *A61M 25/02* (2013.01); *A61B 2046/205* (2016.02); *A61M 2025/0246* (2013.01); *A61M 2025/0266* (2013.01)

(58) Field of Classification Search
CPC .............. A61B 46/00; A61B 2046/205; A61B 2046/234; A61B 2050/002; A61B 46/20; A61M 2025/0246; A61M 2025/0266
USPC .................................................. 604/385.05
See application file for complete search history.

(56) References Cited

U.S. PATENT DOCUMENTS

| 4,324,237 | A |   | 4/1982  | Buttaravoli |
| 4,875,473 | A |   | 10/1989 | Alvarez |
| 5,086,764 | A | * | 2/1992  | Gilman ............... A61F 13/0203 128/888 |
| 5,344,415 | A |   | 9/1994  | deBusk et al. |
| 5,707,348 | A |   | 1/1998  | Krogh |
| 5,860,420 | A | * | 1/1999  | Wiedner ............... A61B 46/00 128/849 |
| 6,090,076 | A |   | 7/2000  | Lane, Jr. |
| 6,124,521 | A |   | 9/2000  | Roberts |
| 6,132,399 | A |   | 10/2000 | Shultz |
| 6,988,511 | B2 |  | 1/2006  | Tang |
| 8,029,479 | B2 |  | 10/2011 | Guthrie |
| 9,668,822 | B2 | * | 6/2017 | Czajka, Jr. ............. A61B 46/00 |

* cited by examiner

*Primary Examiner* — Deanna K Hall
(74) *Attorney, Agent, or Firm* — Reichel Stohry Dean LLP; Mark C. Reichel; Natalie J. Dean

(57) ABSTRACT

A catheter dressing system for providing enhanced isolation and protection of a catheter site from potential contamination during a surgical procedure includes a dressing adhered to a patient covering a catheter. The dressing has a top layer removably covering a base layer. The base layer adheres to the catheter and the patient. The top layer is fluid impermeable. A surgical drape adhesively engages the top layer more strongly than the top layer is engaged to the base layer wherein removal of the surgical drape separates the top layer from the base layer when the surgical drape is removed leaving the base layer uncontaminated and in place covering the catheter after removal of the surgical drape.

20 Claims, 4 Drawing Sheets

CATHETER DRESSING SYSTEM

CROSS-REFERENCE TO RELATED APPLICATIONS

This application is a continuation in part of application Ser. No. 15/377,164 filed on Dec. 13, 2016.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to catheter site dressing devices and more particularly pertains to a new catheter site dressing device for providing enhanced isolation and protection of a catheter site from potential contamination during a surgical procedure.

BRIEF SUMMARY OF THE INVENTION

An embodiment of the disclosure meets the needs presented above by generally comprising a dressing adhered to a patient covering a catheter. The dressing has a top layer removably covering a base layer. The base layer adheres to the catheter and the patient. The top layer is fluid impermeable. A surgical drape adhesively engages the top layer more strongly than the top layer is engaged to the base layer wherein removal of the surgical drape separates the top layer from the base layer when the surgical drape is removed leaving the base layer uncontaminated and in place covering the catheter after removal of the surgical drape.

a dressing adhered to a patient covering a catheter. The dressing has a top layer removably coupled to a medial layer. A first surface of the medial layer faces away from the top layer. The medial layer is fluid impermeable. A surgical drape adhesively engages the top layer of the dressing when positioned on the patient. The top layer is secured to the surgical drape wherein removal of the surgical drape separates the top layer from the medial layer and the medial layer remains in place coupled to the patient covering the catheter.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
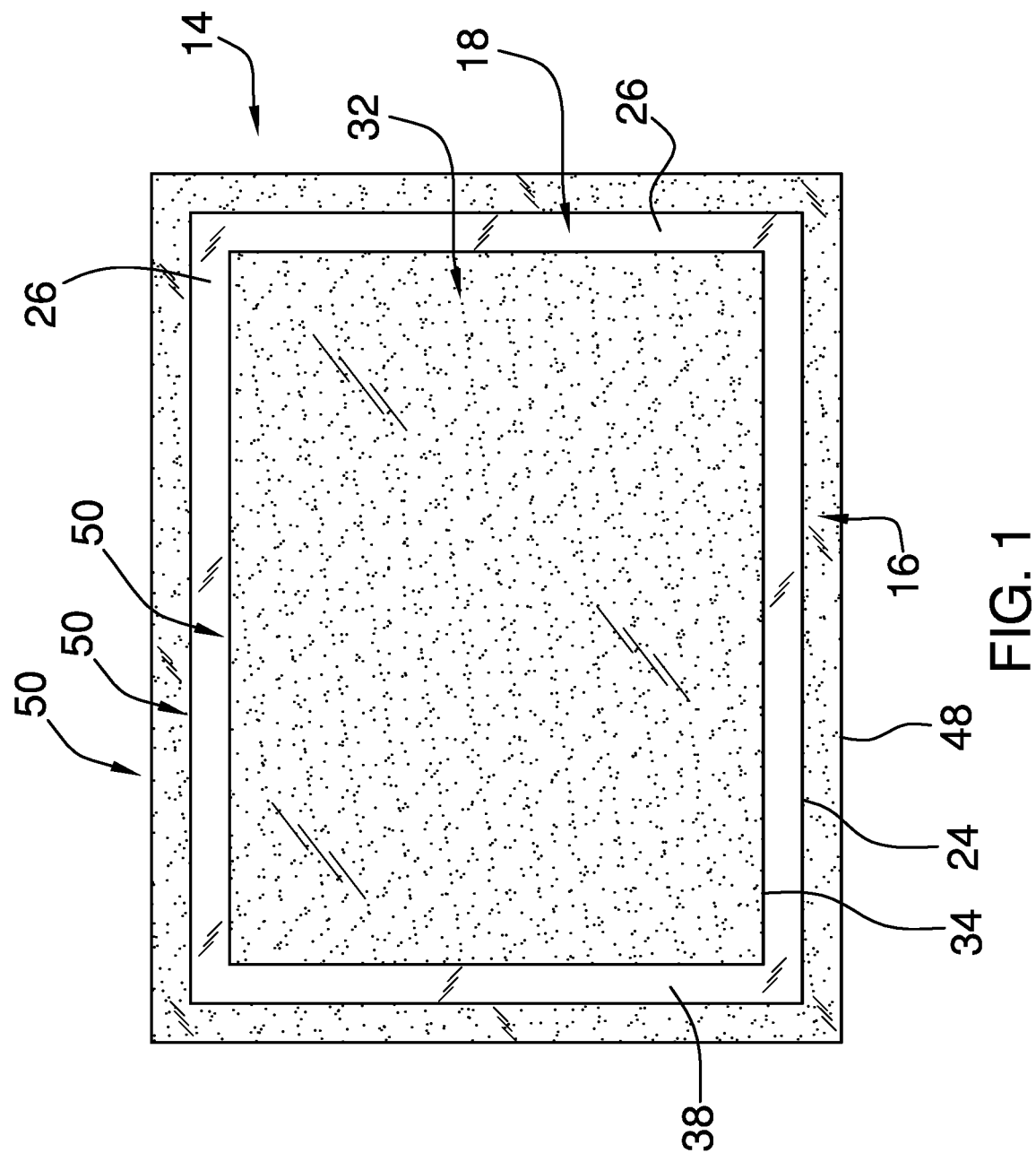
FIG. 1 is a bottom view of a catheter dressing system according to an embodiment of the disclosure.
Figure 2:
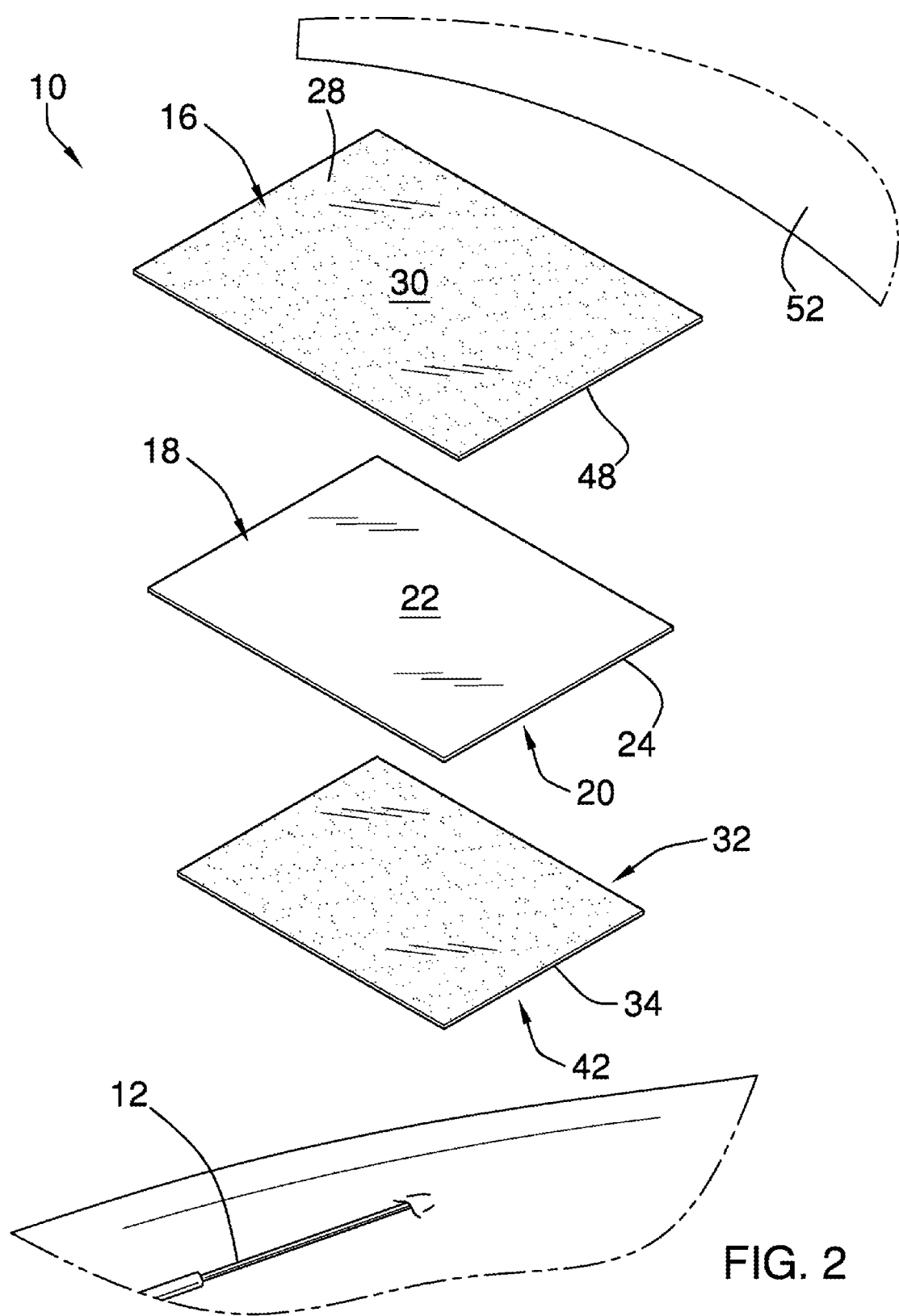
FIG. 2 is a an exploded top front side perspective view of an embodiment of the disclosure.
Figure 3:
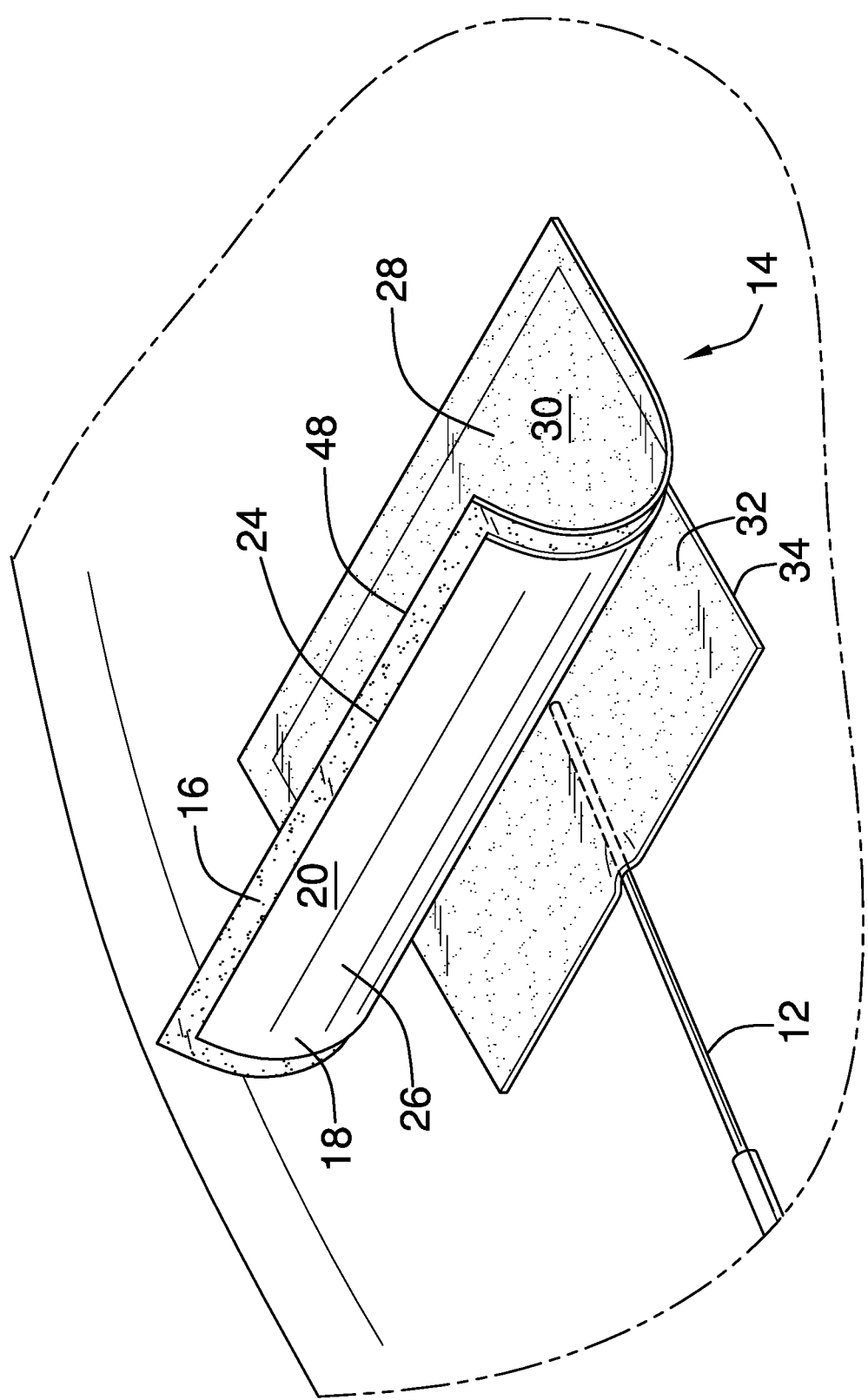
FIG. 3 is a top front side perspective view of an embodiment of the disclosure.
Figure 4:
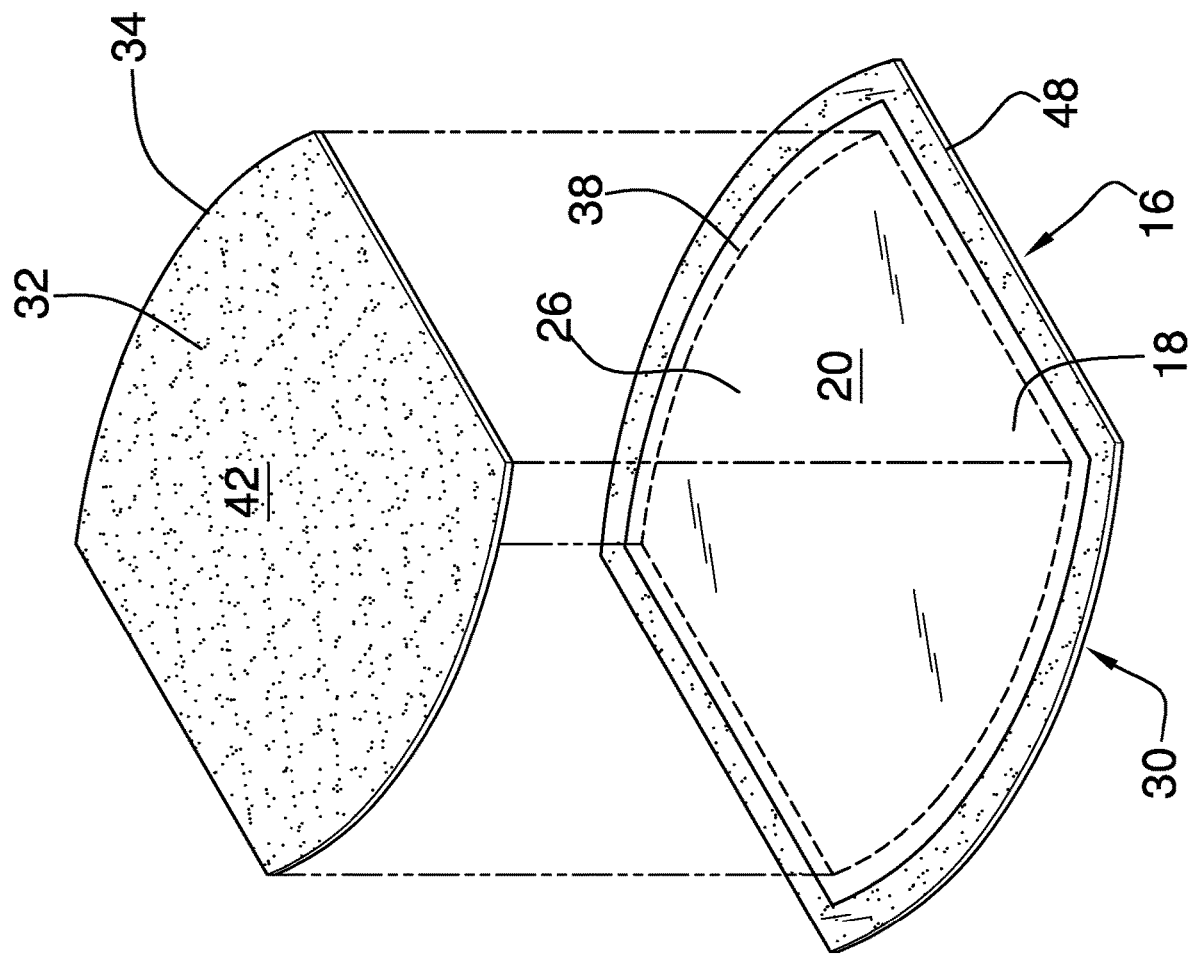
FIG. 4 is a partially exploded bottom front side perspective view of an embodiment of the disclosure.

With reference now to the drawings, and in particular to FIGS. 1 through 4 thereof, a new catheter site dressing device embodying the principles and concepts of an embodiment of the disclosure and generally designated by the reference numeral 10 will be described.

As best illustrated in FIGS. 1 through 4, the catheter dressing system 10 generally comprises a catheter 12 configured to be inserted into a patient in a conventional manner when the patient is undergoing a surgical procedure. A dressing 14 is configured to be adhered to the patient covering the catheter 12 thereby inhibiting the catheter 12 from being contaminated. The dressing 14 has a top layer 16 removably coupled to and covering a base layer 32. The base layer 32 has an adhesive surface 42 facing away from the top layer 16 wherein the base layer 32 is configured for abutting the catheter 12 and the patient wherein the base layer 32 stabilizes a position of the catheter 12 relative to the patient. The top layer 16 is comprised of a fluid impermeable material, of conventional design, such that the top layer 16 inhibits the base layer 32 from being contaminated through the top layer 16. The dressing 14 further comprises a medial layer 18 positioned between the top layer 16 and the base layer 32. The medial layer 18 comprises a first surface 20, a second surface 22 and a perimeter edge 24. The first surface 20 faces away from the top layer 16. The first surface 20 is coupled to the base layer 32 in a conventional manner such as a mild adhesive, static or frictional surfaces, or the like sufficient to hold the dressing 14 together as a coherent single unit until placed on the patient with the base layer 32 covering the catheter 12. The second surface 22 is coupled to the top layer 16 wherein the medial layer 18 couples the top layer 16 to the base layer 32 as described above. Alternatively, if no medial layer 18 is provided, the top layer 16 may be directly coupled to the base layer 32. The medial layer 18 is coupled to the top layer 16 more strongly than to the base layer 32 wherein the medial layer 18 is removed from the base layer 32 with the top layer 16 when the top layer 16 pulled away from the base layer 32.

A peripheral edge 34 of the base layer 32 is inset from the perimeter edge 24 of the medial layer 18 defining an outer portion 38 of the medial layer 18 extending beyond the peripheral edge 34 of the base layer 32 wherein the medial layer 18 completely covers the base layer 32. The perimeter edge 24 of the medial layer 18 is inset from an outermost edge 48 of the top layer 16 wherein the top layer 16 fully covers and extends beyond the perimeter edge 24 of the medial layer 18 to define an outside portion 44 of the top layer 16 extending from the perimeter edge 24 of the medial layer 18. The outside portion 44 of the top layer 16 extends fully around the perimeter edge 24 of the medial layer 18. The top layer 16, the medial layer 18 and the base layer 32 are positioned such that the peripheral edge 34 of the base layer 32, the perimeter edge 24 of the medial layer 18, and the outermost edge 48 of the top layer 16 define a plurality of concentric shapes 50. The first surface 20 between the perimeter edge 24 of the medial layer 18 and the peripheral edge 34 of the base layer 32 is non-adhesive such that the medial layer 18 will not stick to the patient and forms a non-adhesive space around the base layer 32 whereby the top layer 16 is prevented from directly pulling or tugging on the base layer 32 in a direction away from the patient.

A patient adhesive 66, of conventional composition, is positioned on the outside portion 44 of the top layer 16 wherein the top layer 16 is configured for coupling to the patient. The patient adhesive 66 extends fully around the medial layer 18 wherein the top layer 16 is configured to seal to the patient around the medial layer 18 and the base layer 32. A drape adhesive 28 is exposed on the top layer 16 facing away from the base layer 32. A surgical drape 52 is configured to be positioned on the patient in a conventional manner when the patient is undergoing a surgical procedure. The surgical drape 52 adhesively engages the drape adhesive 28 on the top layer 16 of the dressing 14. The top layer 16 is secured to the surgical drape 52 more strongly than to the base layer 32, either directly or through the medial layer 18 if present, wherein removal of the surgical drape 52 separates the top layer 16 from the base layer 32 when the surgical drape 52 is removed from the patient. Thusly, the base layer 32 is configured to be uncontaminated during surgery and remain in place coupled to the patient covering the catheter 12 after removal of the surgical drape 52.

In use, the dressing 14 provides for stabilization of the catheter 12 and protection from contamination while covered by the surgical drape 52 during surgery. Thus, the dressing 14 provides protection to the catheter site throughout an entirety of a surgical procedure with automatic removal of the top layer 16 and exposure of the clean base layer 32 upon removal of the surgical drape 52.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A catheter dressing system facilitating a surgical drape to be removed from a catheter without exposing said catheter to contamination, said system comprising:
    a catheter being configured to be inserted into a patient when the patient is undergoing a surgical procedure;
    a dressing being configured to be adhered to the patient, said dressing covering said catheter thereby inhibiting said catheter from being contaminated, said dressing comprising:
        a top layer;
        a base layer, said base layer having an adhesive surface facing away from said top layer wherein said base layer is configured for abutting said catheter and the patient wherein said base layer stabilizes a position of said catheter relative to the patient; and
        a medial layer positioned between said top layer and said base layer, said medial layer comprising a first surface, a second surface and a perimeter edge, said first surface facing away from said top layer, said first surface being coupled to said base layer, said second surface being coupled to said top layer;
        wherein said top layer being comprised of a fluid impermeable material such that said top layer inhibits said base layer from being contaminated through said top layer;
        wherein said medial layer completely covers said base layer; and
        wherein said top layer completely covers said medial layer;
    a drape adhesive being exposed on said top layer facing away from said base layer; and
    a surgical drape being configured to be positioned on the patient when the patient is undergoing the surgical procedure, said surgical drape adhesively engaging said drape adhesive on said top layer of said dressing, said top layer being secured to said surgical drape more strongly than to said base layer wherein removal of said surgical drape separates said top layer from said base layer when said surgical drape is removed whereby said base layer is configured to be uncontaminated and remain in place coupled to the patient covering said catheter after removal of said surgical drape.

2. The system according to claim 1, further comprising a peripheral edge of said base layer being inset from a perimeter edge of said medial layer defining an outer portion of said medial layer extending beyond said peripheral edge of said base layer wherein said medial layer completely covers said base layer.

3. The system according to claim 1, further comprising said medial layer being coupled to said top layer more strongly than to said base layer wherein said medial layer is removed from said base layer with said top layer when said surgical drape is removed.

4. The system according to claim 1, further comprising a perimeter edge of said medial layer being inset from an outermost edge of said top layer wherein said top layer fully covers and extends beyond said perimeter edge of said medial layer to define an outside portion of said top layer extending from said perimeter edge of said medial layer.

5. The system according to claim 4, further comprising: said outside portion of said top layer extending fully around said perimeter edge of said medial layer; and a patient adhesive positioned on said outside portion of said top layer wherein said top layer is configured for coupling to the patient.

6. The system according to claim 5, further comprising said patient adhesive extending fully around said medial layer wherein said top layer is configured to seal to the patient around said medial layer and said base layer.

7. The system according to claim 1, further comprising said top layer, said medial layer and said base layer being positioned such that a peripheral edge of said base layer, a perimeter edge of said medial layer, and an outermost edge of said top layer define a plurality of concentric shapes.

8. The system according to claim 1, further comprising said first surface between said perimeter edge of said medial layer and said peripheral edge of said base layer being non-adhesive.

9. A catheter dressing system facilitating a surgical drape to be removed from a catheter without exposing said catheter to contamination, said system comprising:
  a catheter being configured to be inserted into a patient when the patient is undergoing a surgical procedure;
  a dressing being configured to be adhered to the patient, said dressing covering said catheter thereby inhibiting said catheter from being contaminated, said dressing comprising:
    a top layer;
    a base layer, said base layer having an adhesive surface facing away from said top layer wherein said base layer is configured for abutting said catheter and the patient wherein said base layer stabilizes a position of said catheter relative to the patient; and
    a medial layer positioned between said top layer and said base layer, said medial layer comprising a first surface, a second surface and a perimeter edge, said first surface facing away from said top layer, said first surface being coupled to said base layer, said second surface being coupled to said top layer;
    wherein said top layer being comprised of a fluid impermeable material such that said top layer inhibits said base layer from being contaminated through said top layer;
    wherein said medial layer completely covers said base layer;
    wherein said top layer completely covers said medial layer; and
    wherein said medial layer being coupled to said top layer more strongly than to said base layer wherein said medial layer is removed from said base layer with said top layer when said surgical drape is removed;
  a peripheral edge of said base layer being inset from said perimeter edge of said medial layer defining an outer portion of said medial layer extending beyond said peripheral edge of said base layer wherein said medial layer completely covers said base layer;
  said perimeter edge of said medial layer being inset from an outermost edge of said top layer wherein said top layer fully covers and extends beyond said perimeter edge of said medial layer to define an outside portion of said top layer extending from said perimeter edge of said medial layer, said outside portion of said top layer extending fully around said perimeter edge of said medial layer, said top layer, said medial layer and said base layer are positioned such that said peripheral edge of said base layer, said perimeter edge of said medial layer, and an outermost edge of said top layer define a plurality of concentric shapes, said first surface between said perimeter edge of said medial layer and said peripheral edge of said base layer being non-adhesive;
  a patient adhesive positioned on said outside portion of said top layer wherein said top layer is configured for coupling to the patient, said patient adhesive extending fully around said medial layer wherein said top layer is configured to seal to the patient around said medial layer and said base layer;
  a drape adhesive being exposed on said top layer facing away from said base layer; and
  a surgical drape being configured to be positioned on the patient when the patient is undergoing the surgical procedure, said surgical drape adhesively engaging said drape adhesive on said top layer of said dressing, said top layer being secured to said surgical drape more strongly than to said base layer wherein removal of said surgical drape separates said top layer from said base layer when said surgical drape is removed whereby said base layer is configured to be uncontaminated and remain in place coupled to the patient covering said catheter after removal of said surgical drape.

10. A catheter dressing system for inhibiting catheter contamination, comprising:
  a dressing, comprising:
    a top layer;
    a base layer having an adhesive surface facing away from the top layer, the base layer configured for abutting a catheter and a patient having the catheter inserted therein so to stabilize a position of the catheter relative to the patient; and
    a medial layer positioned between the top layer and the base layer, the medial layer comprising a first surface, a second surface and a perimeter edge, the first surface facing away from the top layer and coupled to the base layer, and the second surface being coupled to the top layer;
    wherein the top layer comprises of a fluid impermeable material such that the top layer inhibits the base layer from being contaminated through the top layer;
    wherein the medial layer completely covers the base layer; and
    wherein the top layer completely covers the medial layer.

11. The catheter dressing system of claim 10, further comprising:
  the catheter, configured to be inserted into the patient.

12. The catheter dressing system of claim 11, further comprising:
  a dressing configured to be adhered to the patient, the dressing covering the catheter thereby inhibiting the catheter from contamination.

13. The catheter dressing system of claim 10, further comprising:
  a drape adhesive being exposed on the top layer of the dressing facing away from the base layer.

14. The catheter dressing system of claim 13, further comprising:
  a surgical drape being configured to be positioned on the patient when the patient is undergoing the surgical procedure, said surgical drape adhesively engaging the drape adhesive on the top layer of the dressing, the top layer being secured to the surgical drape more strongly than to said base layer, wherein removal of the surgical drape separates the top layer from a remainder of the dressing when the surgical drape is removed, and whereby the base layer is configured to be uncontaminated and remain in place coupled to the patient covering the catheter after removal of the surgical drape.

15. The catheter dressing system of claim 13, wherein the medial layer is coupled to the top layer more strongly than to the base layer such that the medial layer is removed from the base layer along with the top layer when a surgical drape coupled to the top layer of the dressing is removed.

16. The catheter dressing system of claim 13, wherein the perimeter edge of the medial layer is inset from an outermost edge of the top layer such that the top layer fully covers and extends beyond the perimeter edge of the medial layer to define an outside portion of said the layer extending from the perimeter edge of the medial layer.

17. The catheter dressing system of claim 16, wherein the outside portion of the top layer fully extends around the perimeter edge of the medial layer, and wherein a patient adhesive is positioned on the outside portion of the top layer so that the outside portion of the top layer is configured for coupling to the patient.

18. The catheter dressing system of claim 13, configured so that when the dressing is positioned upon the catheter and the patient so to stabilize the catheter, the dressing also inhibits contamination of the catheter while also being configured to couple to a surgical drape.

19. The catheter dressing system of claim 18, wherein when the surgical drape is coupled to the dressing, removal of the surgical drape from the dressing removes the top layer of the dressing and optionally removes the medial layer of the dressing such that the base layer remains positioned upon the catheter and the patient.

20. The catheter dressing system of claim 13, wherein the top layer, the medial layer, and the base layer are positioned relative to one another such that a peripheral edge of the base layer, a perimeter edge of the medial layer, and an outermost edge of the top layer define a plurality of concentric shapes.

\* \* \* \* \*